United States Patent [19]

Sitar

[11] Patent Number: 4,846,805
[45] Date of Patent: Jul. 11, 1989

[54] CATHETER INSERT DEVICE

[75] Inventor: Dennis L. Sitar, Trabuco Canyon, Calif.

[73] Assignee: ICU Medical, Inc., Mission Viejo, Calif.

[21] Appl. No.: 128,740

[22] Filed: Dec. 4, 1987

[51] Int. Cl.⁴ ............................................. A61M 5/00
[52] U.S. Cl. .................................. 604/165; 604/198; 604/110
[58] Field of Search ............................... 604/164–169, 604/162, 198, 197, 110

[56] References Cited

U.S. PATENT DOCUMENTS

| Re. 27,797 | 10/1973 | Sorenson et al. | 604/162 |
|---|---|---|---|
| 2,571,653 | 10/1951 | Bastien . | |
| 2,925,083 | 2/1960 | Craig . | |
| 3,134,380 | 5/1964 | Armao . | |
| 3,356,089 | 12/1967 | Francis . | |
| 3,380,448 | 4/1968 | Sadove et al. . | |
| 3,406,687 | 10/1968 | Moyer . | |
| 3,536,073 | 10/1970 | Farb | 604/162 |
| 3,572,334 | 3/1971 | Petterson | 604/162 X |
| 3,658,061 | 4/1972 | Hall . | |
| 3,890,971 | 6/1975 | Leeson et al. . | |
| 3,943,927 | 3/1976 | Norgren . | |
| 4,026,287 | 5/1977 | Haller . | |
| 4,170,993 | 10/1979 | Alvarez . | |
| 4,329,989 | 5/1982 | Dallons et al. . | |
| 4,373,526 | 2/1983 | Kling . | |
| 4,425,120 | 1/1984 | Sampson et al. . | |
| 4,507,117 | 3/1985 | Vining et al. . | |
| 4,553,962 | 11/1985 | Brunet . | |
| 4,631,057 | 12/1986 | Mitchell . | |
| 4,737,144 | 4/1988 | Chokai . | |

FOREIGN PATENT DOCUMENTS 1541417 10/1968 Canada .
689751 6/1964 France .

Primary Examiner—Stephen C. Pellegrino
Attorney, Agent, or Firm—Knobbe, Martens, Olson & Bear

[57] ABSTRACT

Disclosed is a catheter insert device 10 employing a collection tube 12 having a conical end 18 with a needle 16 extending therefrom. A catheter 20 is removably mounted on the conical end 18 and is pushed off this end by a guard member 14 mounted to move along the longitudinal axis of the collection tube 12. Locking means 60 and 48 between the guard member and the collection tube permanently lock the guard member 14 in an extended position covering the tip 16a of the needle 16 after the catheter 20 has been inserted into the body 21 of a patient.

14 Claims, 3 Drawing Sheets

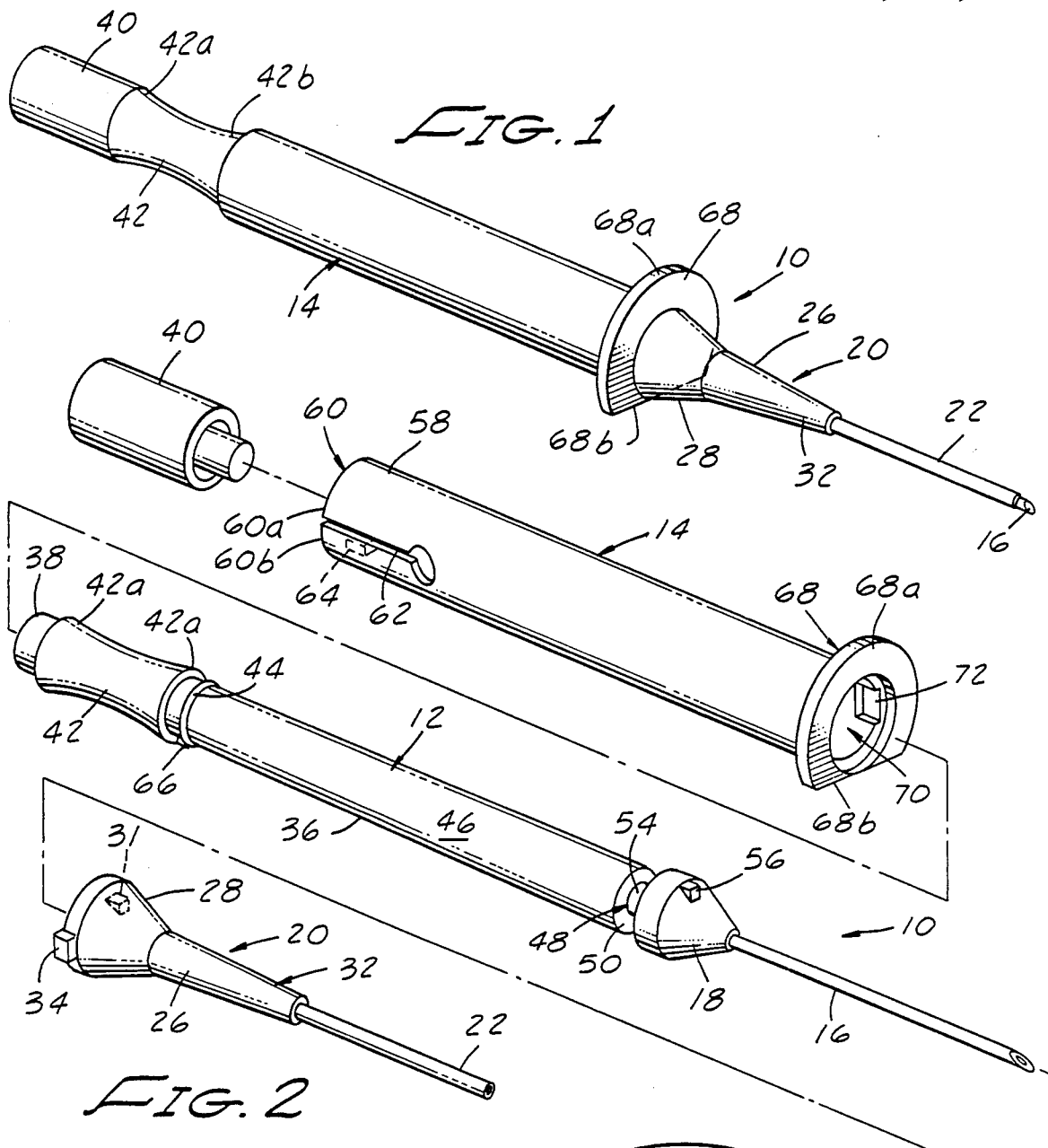
FIG. 1
FIG. 2
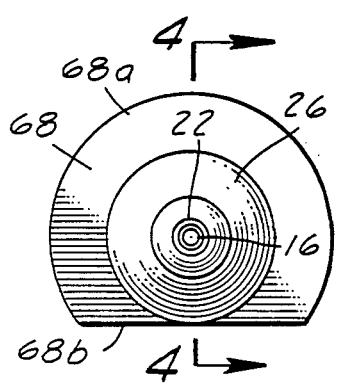
FIG. 3
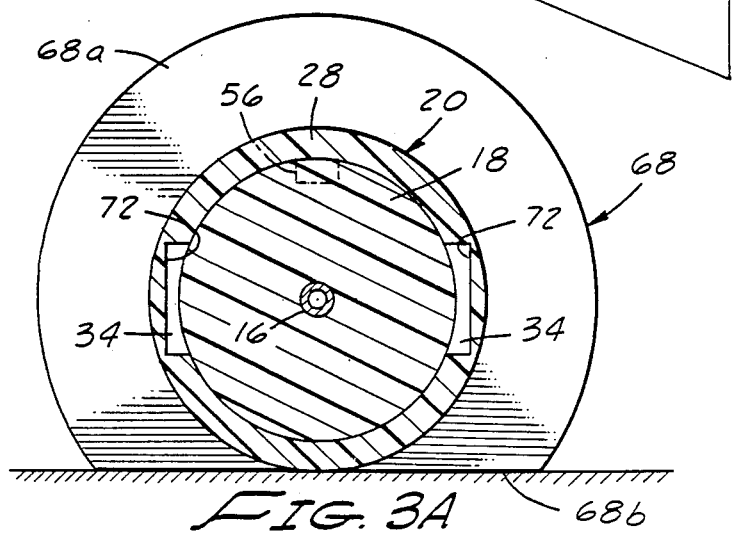
FIG. 3A

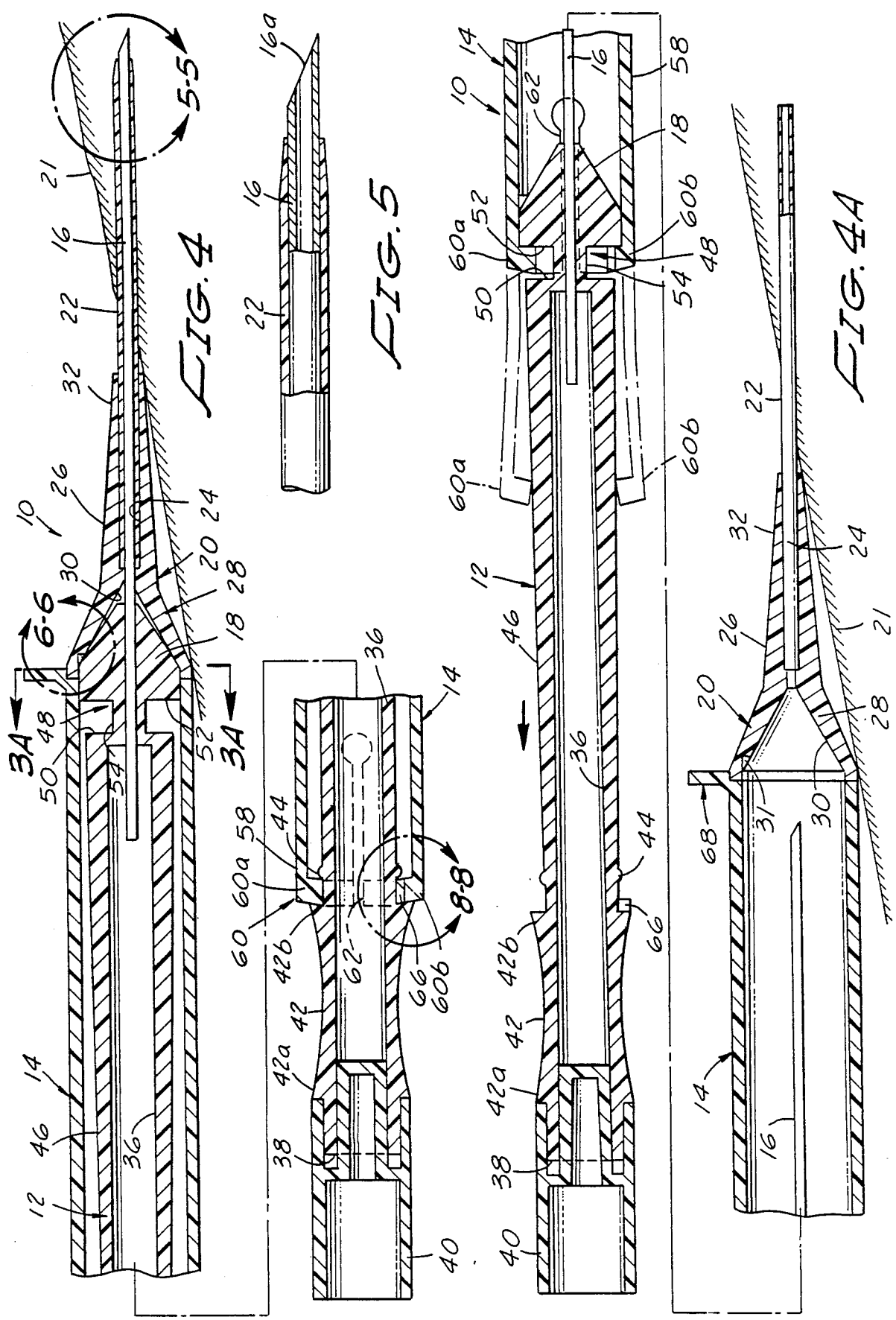

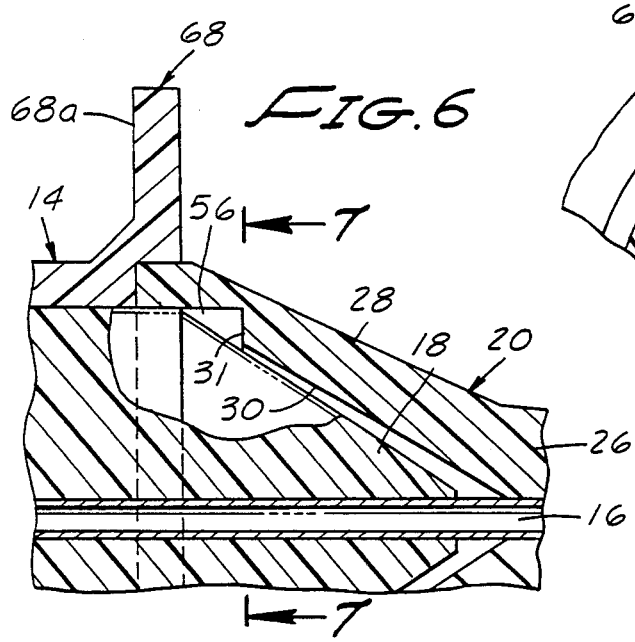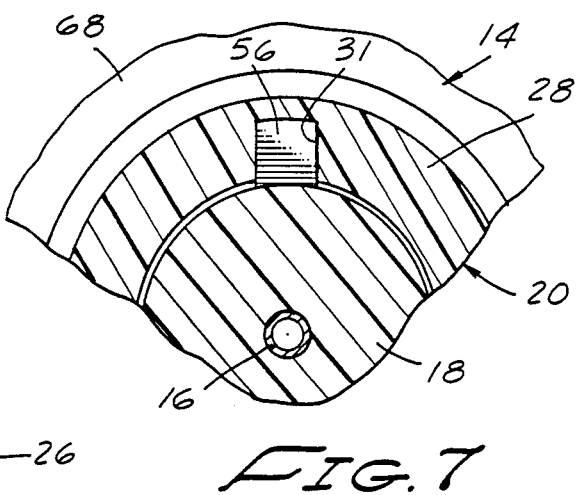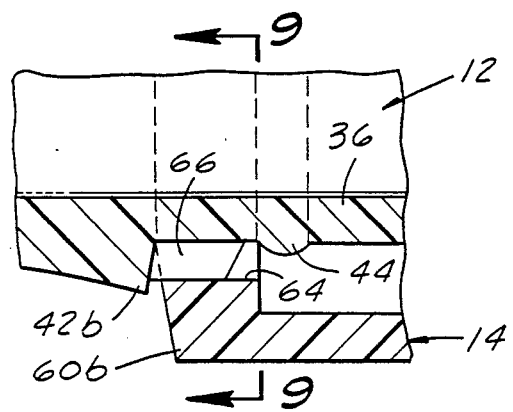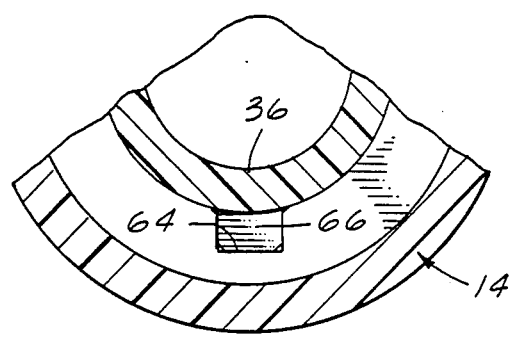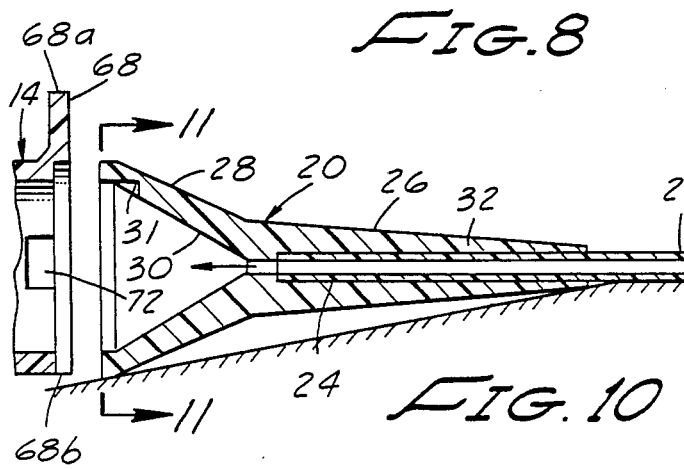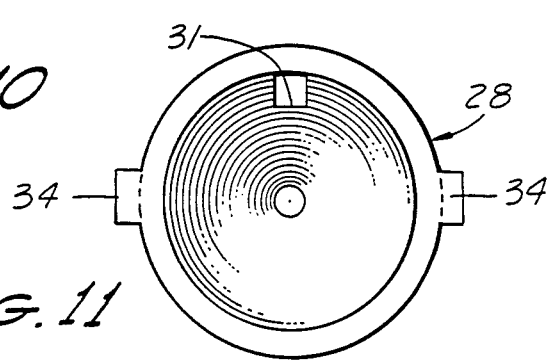

CATHETER INSERT DEVICE

BACKGROUND OF THE INVENTION

1. Field of the Invention

This invention relates to a catheter insert device, and particularly to such a device which has a guard to prevent accidental needle sticks.

2. Background Discussion

Catheters are commonly employed to facilitate administering medication to patients. They usually include an elongated tubular implant section which is inserted into the body of the patient and a connector section which extends from the body of the patient and allows the catheter, for example, to be connected to an intravenous administration set. The typical way of inserting a catheter into the body of a patient is to mount the catheter on a needle, with the needle shaft extending through the tubular implant section. The tip of the needle protrudes outwardly from the end of the implant section, allowing the needle with the catheter to be forced, for example, into the vein of the patient. The catheter is then pushed off the needle shaft as the needle is withdrawn, with the implant section of the catheter remaining in the interior of the vein and the connector section extending outwardly. The connector section usually includes a luer lock which allows the catheter to be securely connected to the intravenous administration set.

SUMMARY OF THE INVENTION

The present invention is a catheter insert device which provides greater safety and convenience to the user. It includes a guard member that moves from a retracted position to an extended position upon withdrawal of the needle after insertion of the catheter to cover the tip of the needle. This guard is permanently locked in position, thereby preventing needle sticks.

There are several features of this invention which contribute to its safety and convenience, no single one of which is solely responsible for these desirable attributes. Without limit in the scope of this invention as expressed by the claims, its more prominent features will now be discussed briefly. After considering this discussion, and particularly after reading the section of this application entitled DETAILED DESCRIPTION OF THE PREFERRED EMBODIMENT, one will understand how the features of this invention provide the attributes of safety and convenience.

The first feature of this invention is the use of a collection tube to collect any body fluid, such as blood, from the patient as the needle enters the body of the patient. This collection tube has a hollow interior with the needle extending outwardly from the forward end of the tube. The needle is generally disposed along the longitudinal axis of the tube, with the hollow shaft of the needle being coincidental with the longitudinal axis of the tube. The guard member is mounted telescopically on the collection tube and adapted to move from a retracted position to an extended position covering the tip of the needle upon withdrawal of the needle from the body of the patient.

The second feature of this invention is that the collection tube has a forward end of a generally conical configuration. This is desirable because the connector section of the catheter generally has a conical recess. The catheter is mounted on this forward end of the collection tube so that the conical end of the tube is received within the conical recess of the catheter. Thus, the catheter is firmly, but removably mounted on the forward end of the tube. The needle extends outwardly from this conical forward end, extending through the apex of the cone into and through the implant section of the catheter.

The third feature of this invention is the use of a generally tubular guard member which is mounted concentrically with the collection tube so that the longitudinal axis of the guard member and the longitudinal axis of the collection tube coincide. There are interlocking means between the guard member and collection tube which prevent the guard member from rotating relative to the collection tube when the guard member is in the retracted position. There are also interlocking means between the catheter and the collection tube which prevent rotation of the catheter relative to the needle when the catheter is mounted on the conical, forward end of the collection tube.

The fourth feature of this invention is the use of a flange at the forward end of the guard member which engages the catheter. This flange has a raised section which preferably includes a groove which receives a portion of the catheter when the catheter is mounted on the conical, forward end of the collection tube. When one pushes against the flange, the guard pushes the catheter off the shaft of the needle. The flange has a flat section that enables the catheter inserter to rest generally flush with the body of the patient during insertion of the catheter. This is desirable in order to maintain the angle of entry of the needle into the body of the patient at a minimum. The tip of the needle is beveled and the flat section is opposite the beveled segment of the needle.

The fifth feature of this invention is the employment of locking means which permanently lock the guard member in the extended position after the needle has been withdrawn from the body of the patient. The locking means preferably includes a locking element carried on the guard member and another locking element carried on the collection tube. These locking elements interact when the guard has been moved to the extended position to permanently lock the guard in the extended position. Preferably, the locking element on the guard includes a collar having two segments which allow the collar to expand outwardly as the guard member moves between the retracted and extended positions. The exterior of the collection tube is generally a cylindrical ramp section over which the collar rides to expand the collar segments outwardly as the guard member moves between its two positions. The ramp section terminates in a groove into which the collar segments snap into locking engagement when the guard member has been moved to the extended position.

BRIEF DESCRIPTION OF THE DRAWING

The preferred embodiment of this invention illustrating all of its features will now be discussed in detail in connection with the accompanying drawing, wherein like numerals indicate like parts, and in which:

FIG. 1 is a perspective view of the catheter insert device of the present invention.

FIG. 2 is an exploded, perspective view of the catheter insert device shown in FIG. 1.

FIG. 3 is an end view of the cathether insert device of this invention as viewed from the needle end.

FIG. 3A is a cross-sectional view taken along line 3A—3A of FIG. 4.

FIG. 4 is a cross-sectional view taken along line 4—4 of FIG. 3, showing the needle of the insert device inserted into the body of a patient.

FIG. 4A is the same view as shown in FIG. 4 except that the needle has been withdrawn from the body of the patient and the guard member moved to the extended position covering the tip of the needle.

FIG. 5 is an enlarged, fragmentary view of the beveled end of the needle taken along line 5—5 of FIG. 4.

FIG. 6 is an enlarged, fragmentary view taken along line 6—6 of FIG. 4, showing the interlocking means which prevents relative rotation between the catheter and collection tube.

FIG. 7 is a cross-sectional view taken along line 7—7 of FIG. 6.

FIG. 8 is an enlarged, fragmentary view taken along line 8—8 of FIG. 4, showing the interlocking means which prevents relative rotation between the guard member and the collection tube.

FIG. 9 is a cross-sectional view taken along line 9—9 of FIG. 8.

FIG. 10 is a cross-sectional view showing the disconnection between the catheter and the insert device after insertion of the catheter in the body of the patient.

FIG. 11 is a cross-sectional view taken along line 11—11 of FIG. 10.

DESCRIPTION OF THE PREFERRED EMBODIMENT

As shown in FIGS. 1 and 2, the catheter insert 10 device of this invention includes a collection tube 12, a guard member 14 mounted on the collection tube, and a needle 16 extending outwardly from the forward conical end 18 of the collection tube. The collection tube 12, and preferably the guard 14, are made of a transparent material, such as a clear plastic, so that one may observe blood filling the tube upon insertion of a catheter 20 mounted on the tube. The catheter 20, which is of conventional design, is carried on the forward end 18, ready to be inserted into the body 21 of the patient. This catheter 20 includes a generally elongated hollow tubular implant section 22 and secured to the rear end 24 of this implant section is a connector section 26, including an rear outwardly tapered end 28 having a conical recess 30 therein and a forward inwardly tapered section 32 in which the implant section is lodged and securely bonded thereto. The tapered end 28 is conical and has a pair of conventional Luer Locks 34 (FIG. 2) to enable the catheter 20 to be connected to an intravenous administration set once it has been inserted into the body 21 of the patient. In the wall of the recess 30 is a keyway 31, which interacts with a key 56 carried by the collection tube 12.

The collection tube 12 has a hollow interior defined by a generally cylindrical wall 36 having an open rear end 38 in which a breather plug 40 is inserted. The breather plug 40 allows air to escape from the tube 12 as it fills with blood, but provides a barrier so blood does not pass through the plug. The rear end 38 has a stop element 42 which limits the inward movement of the plug 40. This stop element 42 has opposed raised ends 42a and 42b. End 42a engages the plug 40 and end 42b engages the guard member 14 to limit the movement of the guard member in the direction of the plug 40. Adjacent this stop element 42 is an annular rib 44 which runs about the exterior surface of the wall 36. The wall 36 expands outwardly from the rear end 38 to provide a conical type ramp section 46 which terminates at an annular groove 48 adjacent the forward conical end 18. As shown in FIGS. 4 and 4a, the groove 48 has a generally flat rear shoulder 50 and a flat forward shoulder 52 which are generally parallel to each other. These shoulders 50 and 52 terminate in a floor section 54. The forward shoulder 52 ends at the wall 36 of the collection tube adjacent the conical end 18. A key 56 extends outwardly from the surface of the conical end 18, which is received in the keyway 31 to interlock with the catheter 20 and prevent rotation of the catheter about the shaft of the needle 16 while mounted on the conical end.

The guard member 14 is a generally hollow, cylindrical, tubular structure made of a transparent material to allow observation of blood flowing into the tube 12. Other means, such as a window in the guard, could also be used for this purpose. The rear end 58 of the guard member 14 has a collar member 60 consisting of two segments 60a and 60b formed by two opposed teardrop slits 62 (only one shown) in the wall of the guard. The slits 62 enable the two segments 60a and 60b of the collar member 60 to expand outwardly as the guard member 14 moves from the retracted position shown in FIG. 4 to the extended position shown in FIG. 4A. There is a keyway 64 in the one collar segment 60b which interacts with a key 66 extending from the shoulder. The key 66 is inserted into the keyway 64 when the guard member 14 is in the retracted position shown in FIGS. 4 and 6, thus preventing rotation of the guard member about the longitudinal axis of the collection tube 12 when the guard member is in the retracted position. Surrounding the open mouth 70 of the guard member 14 is a flange 68 having a generally semi-circular configuration. The semi-circular portion 68a of the flange 68 is raised, extending generally at a right angle to the needle 16. There is a flat edge 68b of the flange 68 which is adapted to rest against the body 21 of the patient when the catheter 20 is being inserted. As best shown in FIG. 5, the tip 16a of the needle 16 is beveled and the flat edge 68b is opposite the beveled segment of the needle tip. At the mouth 70 are two opposed indentations 72 (FIGS. 2 and 3A) which receive the Luer Locks 34 when the catheter 20 is seated on the conical end 18 of the collection tube 12.

OPERATION

The catheter insert device 10 of this invention is very convenient to use. With the catheter 20 mounted on the conical end 18 of the collection tube 12 as shown in FIG. 4, the needle 16 is inserted into the body 21 of the patient, for example in a vein, and then the guard member 14 is moved from the retracted position into the extended position. The nurse will know that the needle is in the vein when she or he observes blood flowing into the collection tube 12. The nurse accomplishes this by simply pushing against the flange 68. As this is done, the collar member 60 first rides over the annular rib 44, moving along the exterior of the wall 36, riding on the ramp section 46 to expand the segments 60a and 60b outwardly as the guard member 14 to moves forward pushing the catheter 20 off the shaft of the needle 16 into the body 21 of the patient. When the collar segments 60a and 60b are opposite the annular groove 48, the two segments snap inwardly so that they are lodged firmly in the groove, locking the guard member 14 permanently in the extended position. The rib 44 serves to hold the guard member 14 in the retracted position shown in FIG. 4 until the nurse applys force to the guard member. The key 56 inserted into the keyway 31 proves interlocking means to prevent relative rotation of the catheter and the collection tube 12 while the catheter is seated on the conical end 18, and the key 66 inserted into the keyway 64 provides interlocking means to prevent relative rotation of the guard member 14 and collection tube 12 while the guard member is in the retracted position.

When the nurse has moved the guard member 14 to the extended position shown in FIG. 4A, the device 10 is separated from the catheter by simply moving the device rearwardly as shown in FIG. 10, leaving the catheter firmly implanted in the body 21 of the patient. The guard member 14 is locked permanently in the extended position, covering the tip 16a of the needle 16. The mouth 70 of the guard member is restricted in diameter so that the tip of the little finger of a typical user could not b inserted into this open mouth and the tip 16a of the needle is displaced inwardly from the open mouth. Thus, the guard member 14 prevents accidental needle sticks.

SCOPE OF THE INVENTION

The above description presents the best mode contemplated of carrying out the present invention. The combination of features illustrated provide the safety and convenience of this invention. This invention is, however, susceptible to modifications and alternate constructions from the embodiment shown in the drawing and described above. Consequently, it is not the intention to limit it to the particular embodiment disclosed. On the contrary, the intention is to cover all modifications and alternate constructions falling within the scope of the invention as generally expressed by the following claims.

I claim:

1. A device for inserting a catheter into the body of a patient, including:
    a collection tube for collecting body fluids of the patient;
    said collection tube having one end on which the catheter is mounted;
    said one end having extending therefrom a needle, with the needle having a tip adapted to extend through the catheter;
    a guard member mounted on the collection tube and movable along the tube between a retracted position where the tip of the needle is exposed and an extended position where the guard member covers said tip; and
    locking means for locking the guard member to the collection tube in the extended position; wherein the movement of the guard from the retracted to the extended position pushes the catheter off of the needle.

2. The device of claim 1 wherein the guard member is telescopically mounted on the collection tube, and the tube is made of a transparent material.

3. The device of claim 2 where there are interlocking means between the guard member and the collection tube which prevents relative rotation between the tube and guard member.

4. The device of claim 1 wherein the collection tube has a conical forward end which is inserted into the catheter.

5. The device of claim 4 wherein there are interlocking means between the collection tube and catheter which prevents relative rotation between the tube and catheter.

6. A device for inserting a catheter into the body of a patient as in claim 1, further comprising means on the collection tube for releasably retaining the guard member in the retracted position.

7. A device for inserting a catheter into the body of a patient, including
    a collection tube for collecting body fluids of the patient,
    said collection tube having one end on which the catheter is mounted,
    said one end having extending therefrom a needle, with the needle having a tip extending through the catheter, said tip having a beveled segment,
    a tubular guard member mounted concentrically on the collection tube and movable along the tube between a retracted position where the tip of the needle tip is exposed and an extended position where the guard member covers said needle tip,
    said guard member having at one end a flange element with a raised section and a flat section adapted to rest against the body of the patient during insertion of the catheter, said flat section being opposite the beveled segment of the needle tip,
    said flange element engaging the catheter and being adapted to push the catheter off the needle as the guard member moves between the retracted and extended positions, and
    locking means for permanently locking the guard member in the extended position, said locking means having one locking element carried by the guard member and another locking element carried by the collection tube.

8. The device of claim 7 wherein the locking means carried by the guard member comprises a collar member at the end of the guard member opposite the end having said flange element and an annular groove in the tube adjacent the flange element, said tube having a ramp section leading to the groove and said collar member expanding outwardly as it rides over the ramp section upon being moved between a retracted and extended position and baised to snap into the groove and lock the guard member permanently in the extended position.

9. The device of claim 8 wherein there is a rib element adjacent the end of the tube opposite said one end where the catheter is mounted, said rib element holding the guard member in the retracted position until moved manually to the extended position.

10. In combination,
    a catheter having an elongated, generally cylindrical hollow implant section adapted to be lodged in the body of a patient, and a connector section from which the implant section extends outwardly, said connector section having an end including a generally conical recess, and
    a catheter insert device including
    a collection tube for collecting body fluids of a patient, said collection tube having a generally conical end over which the catheter fits, with said conical end being received in the conical recess in the connector section of the catheter,
    a needle extending outwardly from the conical end of the collection tube and having a hollow shaft extending through the implant section of the catheter, with body fluids from the patient flowing through the hollow shaft and into the collection tube, said shaft having a first end in communication with the tube so that said body fluids flow into the tube and a second end which has a beveled segment that extends beyond the implant section of the catheter, a tubular guard member mounted on the collection tube and concentric therewith and movable lengthwise along the body of the tube between a retracted position where the needle tip is exposed and an extended position where the guard member covers said tip, said guard member having a forward end with a flange element thereat having a raised section which engages the connector section of the catheter and a flat section adapted to rest against the body of the patient, said flat section being opposite the beveled segment of the needle tip, first interlocking means between the catheter and the collection tube which prevents the catheter from rotating relative to the needle while said catheter is mounted on the conical end of the tube, second interlocking means between the guard member and the collection tube which prevents the guard member from rotating relative to the tube while said guard member is in the retracted position, and locking means between the guard member and the collection tube for permanently locking the guard member in the extended position.

11. The combination of claim 10 wherein the locking means includes an expandable collar member that snaps into locking engagement with a groove in the collection tube adjacent the conical end of said tube.

12. A device for inserting a catheter into the body of a patient, including a collection tube with a needle extending outwardly therefrom and the catheter carried on the needle, a guard member mounted telescopically on the tube and movable along the tube between a retracted position and an extended position, said guard member having a forward end engaging the catheter so that when the guard member is moved between the retracted and extended positions it pushes the catheter off the needle, and locking means having one locking element on the tube and another locking element on the guard member, with said locking element interacting to permanently lock the guard member in the extended position as the guard member is moved from the retracted to the extended position.

13. The device of claim 12 wherein the collection tube is made of a transparent material 14. The device claimed in claim 12 and generally illustrated in the drawing.

* * * * *